United States Patent
Yamakawa

(10) Patent No.: US 9,750,475 B2
(45) Date of Patent: Sep. 5, 2017

(54) CONTOUR IMAGE GENERATING DEVICE AND NUCLEAR MEDICINE DIAGNOSIS APPARATUS

(71) Applicant: SHIMADZU CORPORATION, Kyoto-shi, Kyoto (JP)

(72) Inventor: Yoshiyuki Yamakawa, Kyoto (JP)

(73) Assignee: SHIMADZU CORPORATION, Kyoto (JP)

( * ) Notice: Subject to any disclaimer, the term of this patent is extended or adjusted under 35 U.S.C. 154(b) by 0 days.

(21) Appl. No.: 15/034,148

(22) PCT Filed: Nov. 5, 2013

(86) PCT No.: PCT/JP2013/079900
§ 371 (c)(1),
(2) Date: May 3, 2016

(87) PCT Pub. No.: WO2015/068204
PCT Pub. Date: May 14, 2015

(65) Prior Publication Data
US 2016/0278726 A1    Sep. 29, 2016

(51) Int. Cl.
*G01T 1/164*    (2006.01)
*A61B 6/00*    (2006.01)
(Continued)

(52) U.S. Cl.
CPC ............ *A61B 6/5217* (2013.01); *A61B 6/037* (2013.01); *A61B 6/502* (2013.01); *A61B 6/5205* (2013.01);
(Continued)

(58) Field of Classification Search
None
See application file for complete search history.

(56) References Cited

U.S. PATENT DOCUMENTS

| 2009/0285460 A1* | 11/2009 | Ishikawa | G06K 9/48 382/128 |
| 2010/0278405 A1* | 11/2010 | Kakadiaris | G06F 19/3431 382/131 |
| 2011/0142308 A1* | 6/2011 | Ishikawa | G06T 3/0093 382/128 |

FOREIGN PATENT DOCUMENTS

JP    2003-294843 A    10/2003

OTHER PUBLICATIONS

Chunming Li et al., "Level Set Evolution Without Re-initialization: A New Variational Formulation", CVPR 2005.
(Continued)

*Primary Examiner* — Kiho Kim
(74) *Attorney, Agent, or Firm* — McDermott Will & Emery LLP

(57) ABSTRACT

A contour extracting unit of a contour image generating device performs one-time contour extraction to a two-dimensional reconstruction image by a contour extracting model so as to extract a second shape of a contour from a first shape of a contour. A completion determining unit determines whether or not a rate of change is smaller than a threshold. The rate of change is a ratio of a varied area and a sum of pixel values of pixels in the varied area, the varied area being between the first shape of the contour and the second shape of the contour. When the rate of change is large, a repetitive controller performs control to operate the contour extracting unit and the like again. When the rate of change is small, the repetitive controller performs control to output a two-dimensional contour image containing the second shape of the contour.

7 Claims, 9 Drawing Sheets

(51) Int. Cl.
  *A61B 6/03*  (2006.01)
  *G01T 1/29*  (2006.01)
  *G06T 7/149* (2017.01)
(52) U.S. Cl.
  CPC ............ *G01T 1/2985* (2013.01); *G06T 7/149* (2017.01); *G06T 2207/10104* (2013.01); *G06T 2207/20161* (2013.01); *G06T 2207/30068* (2013.01)

(56) References Cited

OTHER PUBLICATIONS

Search Report and Written Opinion issued in corresponding International Application No. PCT/JP2013/079900, dated Jan. 28, 2014 (w/Partial English Translation).

\* cited by examiner

CONTOUR IMAGE GENERATING DEVICE AND NUCLEAR MEDICINE DIAGNOSIS APPARATUS

CROSS REFERENCE

This application is the U.S. National Phase under 35 U.S.C. §371 of International Application No. PCT/JP2013/079900, filed on Nov. 5, 2013, the disclosure of which Application is incorporated by reference herein.

TECHNICAL FIELD

The present invention relates to a contour image generating device and a nuclear medicine diagnosis apparatus that extract a contour of an imaging target of a subject in accordance with collection data obtained by administering radiopharmaceutical into the subject and detecting radiation emitted from the inside of the subject.

BACKGROUND ART

Examples of currently-used nuclear medicine diagnosis apparatus include a PET (positron emission tomography) apparatus. The PET apparatus reconstructs a tomographic image of a subject only when a plurality of detectors detects two beams of γ-rays coincidently generated due to annihilation of positive electrons (positrons). Moreover, examples of the PET apparatus include a mammography PET apparatus that images the breast of the subject. The mammography PET apparatus includes detectors that surround the breast of the subject. The detectors are disposed closely to the breast of the subject, enhancing detection sensitivity.

The γ-rays detected with the detectors are γ-rays emitted from the inside of the subject to which the radiopharmaceutical is administered in advance. The emitted γ-rays are absorbed in tissue within the subject. Consequently, the PET apparatus performs absorption correction taking into consideration of influences of γ-ray absorption upon generating a PET image (see, for example, Patent Literature 1). The absorption correction is typically performed with data upon imaging with an X-ray CT apparatus and data upon detection with an external source that emits γ-rays. However, it is difficult to provide the X-ray CT apparatus or the external source on the mammography PET apparatus. Accordingly, absorption correction is performed under assumption that the breast of the subject is a single absorber. In this method, a contour of the breast is extracted, and an absorption coefficient equal to that of the breast is assigned in the extracted contour, whereby an absorption coefficient map is generated. Then, the absorption correction is performed based on the generated absorption coefficient map.

A dynamic contour model such as a level set method is used as the method for extracting a contour of an object such as the subject (see, for example, Non-Patent Literature 1). The dynamic contour model is a method of extracting the contour by dynamically changing a closed curve on the image to conform to the contour of the object.

Patent Literature 1: Japanese Unexamined Patent Publication No. 2003-294843A

Non-Patent Literature 1: C. Li, C. Xu, C. Gui, and M. D. Fox, "Level Set Evolution Without Re-initialization: A New Variational Formulation", CVPR 2005

SUMMARY OF INVENTION

Technical Problem

Such contour extraction with the dynamic contour model needs a great repeated number of processes for extracting the contour of the object. Accordingly, an accuracy of the obtained contour varies depending on the number of processes. An operator sets the number of processes, and performs contour extraction by the set number of processes to extract the contour. On the other hand, the operator needs to visually confirm whether or not the contour with high accuracy is obtained. Then, when the obtained contour is smaller than a contour of the object, the number of processes is decreased. When the obtained contour is larger than the contour of the object, the number of processes is increased. In this manner, the contour of the object with high accuracy is obtainable.

On the other hand, when the currently-used mammography PET apparatus adopts the contour extraction with the dynamic contour model as in the Non-Patent Literature 1 for extracting the contour of the breast of the subject, a drawback may arise that the contour with high accuracy fails to be obtainable. That is, by the contour extraction with the dynamic contour model, the contour is extracted using gradient information on a two-dimensional reconstruction image. This causes a shape of the contour to remain at a position at which pixel values of adjacent pixels changes largely. In other words, when the contour of the breast of the subject is clear, the shape of the contour should remain at the contour of the breast contour.

However, a reconstruction image with many statistical noises may cause the contour to remain at a gradient by the noises (i.e., noise portions). Accordingly, the large number of contour extraction processes is needed for obtaining the shape of the contour with high accuracy. Moreover, the breast may contain an object such as tumor at which pixel values of adjacent pixels change more largely than that at the contour of the breast. In this case, when the contour is not extracted by the appropriate number of processes, the shape of the contour to be obtained may enter inside of the contour of the breast. As a result, a contour of the object such as tumor may be extracted as the shape of the contour, leading to an unexpected shape of the contour.

Moreover, when the contour extraction is performed to one image, an operator visually confirms an obtained shape of the contour, and repeatedly sets some of the number of processes, whereby the shape of the contour with high accuracy is obtainable relatively rapidly. However, when the contour extraction is performed to data on the nuclear medicine diagnosis apparatus with a large number of slice pieces, the appropriate number of processes may be different depending on the slice pieces. Accordingly, it takes much time for the operator to visually confirm the shape of the contour for every slice piece. In addition, it is quite difficult to perform the contour extraction while setting the number of processes many times.

The present invention has been made regarding the state of the art noted above, and its one object is to provide a contour image generating device and a nuclear medicine diagnosis apparatus that allow automatic extraction of a contour shape of an imaging target of a subject by the appropriate number of processes accurately without any visual confirmation by an operator.

Solution to Problem

The present invention is constituted as stated below to achieve the above object. One aspect of the present invention provides a contour image generating device. The contour image generating device includes a contour extracting unit, a varied area calculating unit, a pixel value sum calculating unit, a change rate calculating unit, a completion determining unit, and a controller. The contour extracting unit performs one of contour extraction processes that are repeatedly performed by a contour extracting model to a two-dimensional reconstruction image of a subject obtained through detection of radiation emitted from the subject to extract a new second shape of a contour from a first shape of the contour set in advance. The varied area calculating unit calculates a varied area between the first shape of the contour and the second shape of the contour. The pixel value sum calculating unit calculates the sum of pixel values of pixels contained in the varied area. The change rate calculating unit calculates a rate of change that corresponds to a ratio of the varied area and the sum. The completion determining unit determines whether or not the rate of change is smaller than a threshold set in advance. The controller performs control to set the second shape of contour as the first shape of contour and to operate the contour extracting unit, the varied area calculating unit, the pixel value sum calculating unit, the change rate calculating unit, and the completion determining unit again when the completion determining unit determines that the rate of change is larger than the threshold, and performs control to output two-dimensional contour images each containing the second shape of the contour when the completion determining unit determines that the rate of change is smaller than the threshold.

With the contour image generating device according to the aspect of the present invention, the contour extracting unit performs one of the contour extraction processes that are performed repeatedly to the two-dimensional reconstruction image by the contour extracting model, and extracts the new second shape of the contour from the first shape of the contour set in advance. The completion determining unit determines whether or not the rate of change is smaller than the threshold set in advance. The rate of change is calculated as under. That is, the varied area calculating unit calculates the varied area between the first shape of the contour and the second shape of the contour. The pixel value sum calculating unit calculates the sum of pixel values of the pixels contained in the varied area. The change rate calculating unit calculates the rate of change that corresponds to the ratio of the varied area and the sum. A controller performs control to set the second shape of the contour as the first shape of the contour and to operate the contour extracting unit and the like again when the completion determining unit determines that the rate of change is larger than the threshold, and performs control to output the two-dimensional contour image containing the second shape of the contour when the completion determining unit determines that the rate of change is smaller than the threshold.

Specifically, the rate of change that corresponds to the ratio of the varied area and the sum of pixel values of the pixels contained in the varied area has a characteristic to be stabilized within a substantially equal value at every time regardless of data on the two-dimensional reconstruction images. Such a characteristic is used for setting the threshold in advance from a plurality of samples of data obtained in advance. The controller performs control to output the two-dimensional contour image containing the second shape of the contour when the completion determining unit determines that the rate of change is smaller than the threshold. This allows automatic extraction of the contour shape of the imaging target of the subject accurately by the appropriate number of processes without any visual confirmation by the operator.

Moreover, the following is preferred. That is, the contour image generating device according to the aspect of the present invention further includes a process number determining unit that counts the number of contour extraction processes to determine whether or not the number of processes reaches a break number of times. The change rate calculating unit calculates a rate of change for every break number of times that corresponds to a ratio of a total sum of the varied area and the sum. The controller performs control to set the second shape of the contour as the first shape of the contour and to operate the contour extracting unit, the varied area calculating unit, the pixel value sum calculating unit, and the process number determining unit again when the process number determining unit determines that the number of processes fails to reach the break number of times and performs control to reset the number of processes and conduct determination by the completion determining unit when the process number determining unit determines that the number of processes reaches the break number of times, and the controller performs control to set the second shape of the contour as the first contour and operate the contour extracting unit, the varied area calculating unit, the pixel value sum calculating unit, the change rate calculating unit, the process number determining unit, and the completion determining unit again when the completion determining unit determines that the rate of change is larger than the threshold.

In a relationship between the number of processes and the rate of change in the contour extraction, the rate of change may increase and decrease for one-time process because of the statistical noises in the two-dimensional reconstruction image. In this case, if completion determination is performed at every number of processes, the rate of change temporarily decreases largely to be smaller than the threshold, leading to completion of the contour extraction before the rate of change is stabilized. Regarding this, with the aspect of the present invention, the process number determining unit is provided for performing determination for every break number of times, i.e., for plural numbers of processes without completion determination for one-time process. Moreover, the change rate calculating unit calculates the rate of change that corresponds to the ratio of the total sum of varied areas and the sum of pixel values for every break number of times. As a result, the completion determining unit performs determination with the rate of change calculated as an average value for every break number of times. Consequently, this prevents completion of the contour extraction before the rate of change is stabilized by a variation in rate of change for every number of processes, leading to extraction of the shape of the contour accurately by the appropriate number of processes.

In addition, in one embodiment of the contour image generating device according to the aspect of the present invention, the break number of times is variable. That is, when the number of processes reaches the break number of times, a next break number of times may be set different from the previous break number of times. For instance, a relatively large number of processes is set as a break number of times in the number of processes having a large difference between the threshold and the rate of change, whereas a relatively small number of processes is set as a break number of times in the number of processes having a small difference between the threshold and the rate of change. This allows extraction of the shape of the contour accurately by the appropriate number of processes while the number of completion determination is decreased.

Moreover, it is preferred in the contour image generating device according to the aspect of the present invention that the break number of times decreases as the number of processes reaches the break number of times. That is, when the number of processes reaches the break number of times, a next break number of times is set to be smaller than or equal to the previous break number of times. This allows extraction of the shape of the contour accurately by the appropriate number of processes while the number of completion determination is decreased.

Moreover, in one embodiment of the contour image generating device according to the aspect of the present invention, the break number of times is constant. This allows simple completion determination under the same condition.

It is preferred in the contour image generating device according to the aspect of the present invention that the two-dimensional reconstruction image is one of two-dimensional reconstruction images forming a three-dimensional reconstruction image subjected to reconstruction, and that the controller performs control to generate the three-dimensional contour image from a plurality of outputted two-dimensional contour images. For instance, when the contour extraction is performed by a fixed number of processes, the appropriate number of processes is performed to one image, and a large or small number of processes are performed to another image. Regarding this, the aspect of the present invention allows accurate extraction of the shape of the contour by the appropriate number of processes for every two-dimensional reconstruction image (slice piece).

Another aspect of the present invention provides a nuclear medicine diagnosis apparatus. The nuclear medicine diagnosis apparatus includes a detector unit, a data collecting unit, a reconstruction unit, a contour extracting unit, a varied area calculating unit, a pixel value sum calculating unit, a change rate calculating unit, a completion determining unit, and a controller. The detector unit includes a plurality of detectors arranged in a ring shape and detects radiation emitted from a subject. The data collecting unit collects emission data in accordance with the radiation detected with the detector unit. The reconstruction unit reconstructs the emission data to obtain a two-dimensional reconstruction image. The contour extracting unit performs one of contour extraction processes that are repeatedly performed by a contour extracting model to the two-dimensional reconstruction image to extract a new second shape of a contour from a first shape of the contour set in advance. The varied area calculating unit calculates a varied area between the first shape of the contour and the second shape of the contour. The pixel value sum calculating unit calculates the sum of pixel values of pixels contained in the varied area. The change rate calculating unit calculates a rate of change that corresponds to a ratio of the varied area and the sum. The completion determining unit determines whether or not the rate of change is smaller than a threshold set in advance. The controller performs control to set the second contour as the first contour and to operate the contour extracting unit, the varied area calculating unit, the pixel value sum calculating unit, the change rate calculating unit, and the completion determining unit again when the completion determining unit determines that the rate of change is larger than the threshold, and performs control to output a two-dimensional contour image containing the second shape of the contour when the completion determining unit determines that the rate of change is smaller than the threshold.

With the nuclear medicine diagnosis apparatus according to the other aspect of the present invention, the contour extracting unit performs one of contour extraction processes that are performed repeatedly to the two-dimensional reconstruction image by the contour extracting model and extracts the new second shape of the contour from the first shape of the contour set in advance. The completion determining unit determines whether or not the rate of change is smaller than the threshold set in advance. The rate of change is calculated as under. That is, the varied area calculating unit calculates the varied area between the first shape of the contour and the second shape of the contour. The pixel value sum calculating unit calculates the sum of pixel values of the pixels contained in the varied area. The change rate calculating unit calculates the rate of change that corresponds to the ratio of the varied area and the sum. A controller performs control to set the second shape of the contour as the first shape of the contour and operate the contour extracting unit and the like again when the completion determining unit determines that the rate of change is larger than the threshold, and performs control to output the two-dimensional contour image containing the second shape of the contour when the completion determining unit determines that the rate of change is smaller than the threshold.

Specifically, the rate of change that corresponds to the ratio of the varied area and the sum of pixel values of the pixels contained in the varied area has a characteristic to be stabilizes within a substantially equal value at every time regardless of data on the two-dimensional reconstruction image. Such a characteristic is used for setting the threshold in advance from a plurality of samples of data obtained in advance. The controller performs control to output the two-dimensional contour image containing the second shape of the contour when the completion determining unit determines that the rate of change is smaller than the threshold. This allows automatic extraction of the contour shape of the imaging target of the subject accurately by the appropriate number of processes without any visual confirmation by the operator.

Advantageous Effects of Invention

The contour image generating device and the nuclear medicine diagnosis apparatus according to the aspects of the present invention allow automatic extraction of the contour shape of the imaging target of the subject accurately by the appropriate number of processes without any visual conformation by the operator.

EMBODIMENT 1

Figure 1:
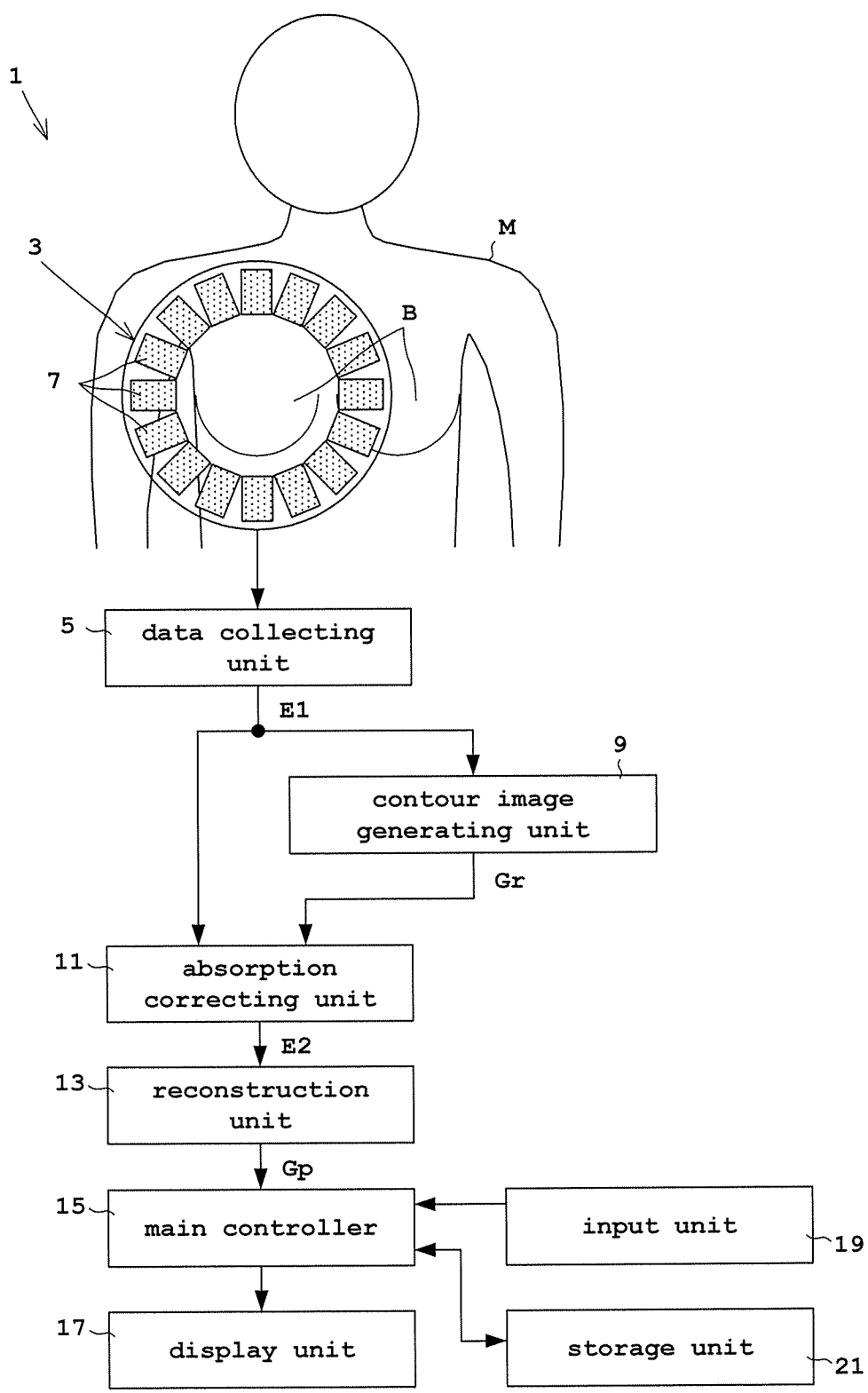
FIG. 1 schematically illustrates a mammography PET apparatus according to Preferred Embodiment 1 of the present invention.

The following describes Preferred Embodiment 1 of the present invention with reference to drawings. In the Embodiment 1, a mammography PET apparatus is to be described as one example of a nuclear medicine diagnosis apparatus. FIG. 1 schematically illustrates the mammography PET apparatus according to the Embodiment 1.

Reference is made to FIG. 1. A mammography PET apparatus 1 includes a detector unit 3 that detects γ-rays emitted from a breast B of a subject M to which radiopharmaceutical is administered, and a data collecting unit 5 that collects emission data E1 in accordance with γ-rays detected with the detector unit 3.

The detector unit 3 includes a plurality of γ-ray detectors 7. The γ-ray detectors 7 are arranged in a ring shape so as to surround the breast B of the subject M as an imaging target. Here, the γ-ray detectors 7 correspond to the detector in the present invention.

The γ-ray detectors 7 each include scintillator blocks, a light guide, and a photomultiplier (each not shown). The scintillator blocks are plural and are arranged in a matrix (e.g., eight rows and eight columns). In addition, the scintillator blocks arranged two-dimensionally include a single-layer structure or a laminated structure with a plurality of layers (e.g., two layers). When the γ-rays enter into the scintillator blocks, the γ-rays are converted into light. The converted light is transmitted from the scintillator blocks via the light guide to the photomultiplier. The photomultiplier converts the transmitted light into electric signals.

The data collecting unit 5 includes a coincidence circuit not shown. The data collecting unit 5 collects an event as the emission data E1 determined coincident in accordance with the electric signals generated from the detected γ-rays and outputted from the detector unit 3. That is, the data collecting unit 5 collects an event as coincident information, the event being only when two γ-ray detectors 7 detect two beams of γ-rays emitted at a straight angle opposite to each other from the subject M for a given period of time. The emission data E1 is collected three-dimensionally, but may be collected two-dimensionally in some cases.

On a subsequent stage of the data collecting unit 5, provided are a contour image generating unit 9 that generates a three-dimensional contour image Gr from the collected emission data E1, the three-dimensional contour image Gr being as an image containing a shape of a contour of the breast B of the subject M, and an absorption correcting unit 11 that generates an absorption coefficient map based on the three-dimensional contour image Or generated by the contour image generating unit 9 and performs absorption correction to the emission data E1 using the absorption coefficient map.

The absorption coefficient map used for the absorption correction is obtained by uniformly assigning an absorption coefficient equal to that for the breast B of the subject M to the inside of the contour of the breast B in the three-dimensional contour image Gr. The absorption coefficient is set in advance. The absorption correcting unit 11 performs the absorption correction to the emission data E1 to generate emission data E2 subjected to the absorption correction. Here, the contour image generating unit 9 corresponds to the contour image generating device in the present invention.

On the subsequent stage of the absorption correcting unit 11, further provided is a reconstruction unit 13 that reconstructs the emission data E2 subjected to the absorption correction to generate a PET image Gp. The reconstruction unit 13 performs reconstruction with a two-dimensional or three-dimensional reconstruction method. For instance, a three-dimensional iterative approximation reconstruction method is used for the reconstruction. Moreover, the absorption correcting unit 11 may be included in a system model of the reconstruction unit 13.

The mammography PET apparatus 1 further includes a main controller 15 that controls en bloc each element of the apparatus 1, a display unit 17 that displays the PET image Gp generated by the reconstruction unit 13, an input unit 19 used for operator's input setting or operation, and a storage unit 21 that stores the PET image Gp and the like. The main controller 15 includes a central processing unit (CPU) and the like. The display unit 17 includes a liquid crystal monitor. The input unit 19 includes a keyboard, and a mouse. The storage unit 21 includes a storage medium such as a ROM (Read-only Memory), a RAM (Random-Access Memory), and a hard disk. The storage medium may be detachable to the mammography PET apparatus 1.

Contour Image Generating Unit

Figure 2:
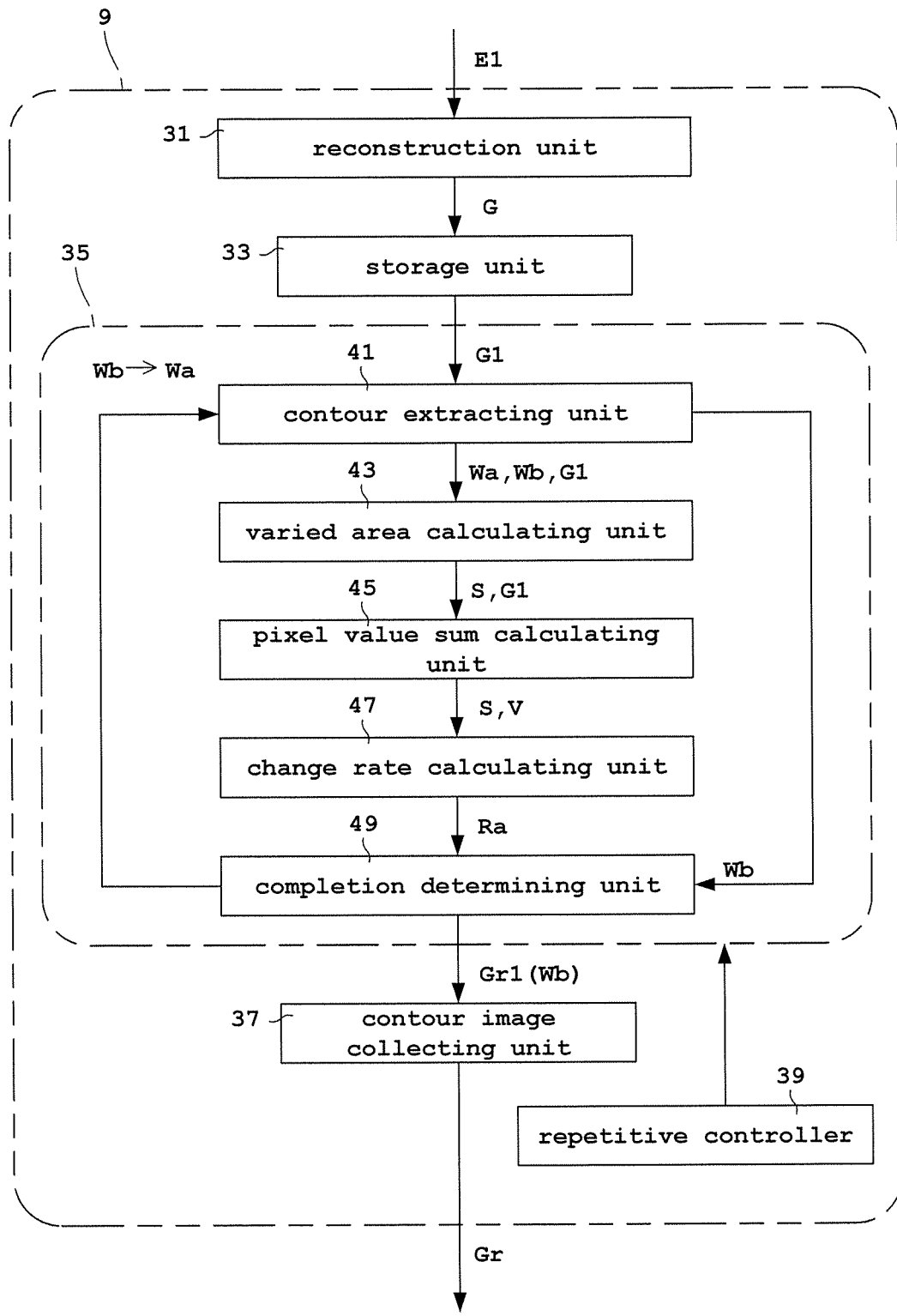
FIG. 2 illustrates a contour image generating unit according to Embodiment 1.

The following describes a concrete configuration of the contour image generating unit 9, which is a characteristic of the present invention. FIG. 2 illustrates the contour image generating unit 9 according to the Embodiment 1. The following firstly describes a brief configuration of the contour image generating unit 9.

The contour image generating unit 9 includes a reconstruction unit 31 that reconstructs the collected emission data E obtained by detecting two beams of γ-rays emitted from the breast B of the subject M to generate a three-dimensional reconstruction image G of the breast B of the subject M, and a storage unit 33 that stores the generated three-dimensional reconstruction image G. A repetitive controller 39, to be mentioned later, performs control to read one of the two-dimensional reconstruction images G1 that form the three-dimensional reconstruction image G stored in the storage unit 33 (see FIG. 3). Moreover, the contour image generating unit 9 further includes a contour determining unit 35 that determines the shape of the contour of the breast B of the subject M in the read-out two-dimensional reconstruction image G1 to output a two-dimensional contour image Gr1, a contour image collecting unit 37 that collects the outputted two-dimensional contour image Gr1 to output a three-dimensional contour image Gr, and the repetitive controller 39 that performs control en bloc to each element of the contour image generating unit 9. The repetitive controller 39 corresponds to the controller in the present invention.

The contour determining unit 35 includes a contour extracting unit 41 that performs one of contour extraction processes that are repeatedly performed with the contour extracting model, and extracts a new a second shape of the contour Wb from a first shape of the contour Wa set in advance in the obtained two-dimensional reconstruction image G1. The contour determining unit 35 further includes a varied area calculating unit 43 that calculates (computes) a varied area S between the first shape of the contour Wa and the second shape of the contour Wb, and a pixel value sum calculating unit 45 that calculates the sum V of pixel values of pixels in the varied area S, and a change rate calculating unit 47 that calculates a rate of change Ra (=S/V) as a ratio of the varied area S and the sum V.

Moreover, the contour determining unit 35 further includes a completion determining unit 49 that determines whether or not the rate of change Ra is smaller than a threshold P set in advance. The repetitive controller 39 performs control to set the second shape of the contour Wb as the first shape of the contour Wa and operate the contour extracting unit 41, the varied area calculating unit 43, the pixel value sum calculating unit 45, the change rate calculating unit 47, and the completion determining unit 49 again when the completion determining unit 49 determines that the rate of change Ra is larger than the threshold P. In addition, the repetitive controller 39 performs control to output the two-dimensional contour image Gr1 containing the second shape of the contour Wb when the completion determining unit 49 determines that the rate of change Ra is smaller than the threshold P.

The following describes the above elements in detail in turn. The reconstruction unit 31 reconstructs the collected emission data E1 obtained by detecting two beams of γ-rays emitted from the breast B of the subject M to generate the three-dimensional reconstruction image G for the breast B of the subject M. Here, the reconstruction is performed with a known method such as a two-dimensional reconstruction method or a three-dimensional reconstruction method. For instance, a combination of a rebinning method or an FORE (Fourier rebinning) method and an iterative approximation image reconstruction method such as an OS-EM (ordered subsets-expectation maximization) method may be used for the reconstruction to the collected three-dimensional emission data E1. Moreover, a list mode three-dimensional DRAMA (dynamic RAMLA) method may be used for the reconstruction.

The contour extracting unit 41 performs one of the contour extraction processes repeatedly conducted with the contour extracting model in each of the two-dimensional reconstruction images G1 that form the three-dimensional reconstruction image G generated by the reconstruction unit 31. The one-time contour extraction process by the contour extracting model corresponds to a process of extracting a new second shape of the contour Wb from the first shape of the contour Wa set in advance. For instance, a level set method or a snake method is used for the contour extracting model. The level set method possesses the following effect relative to the snake method. For instance, if the subject M is small, both of breasts B may be imaged. If a plurality of objects is present in the image in such a case above, the snake method allows no individual extraction of the shape of the contour for its process mechanism. In contrast to this, the level set method allows individual extraction of the shape of the contour.

Figure 4:
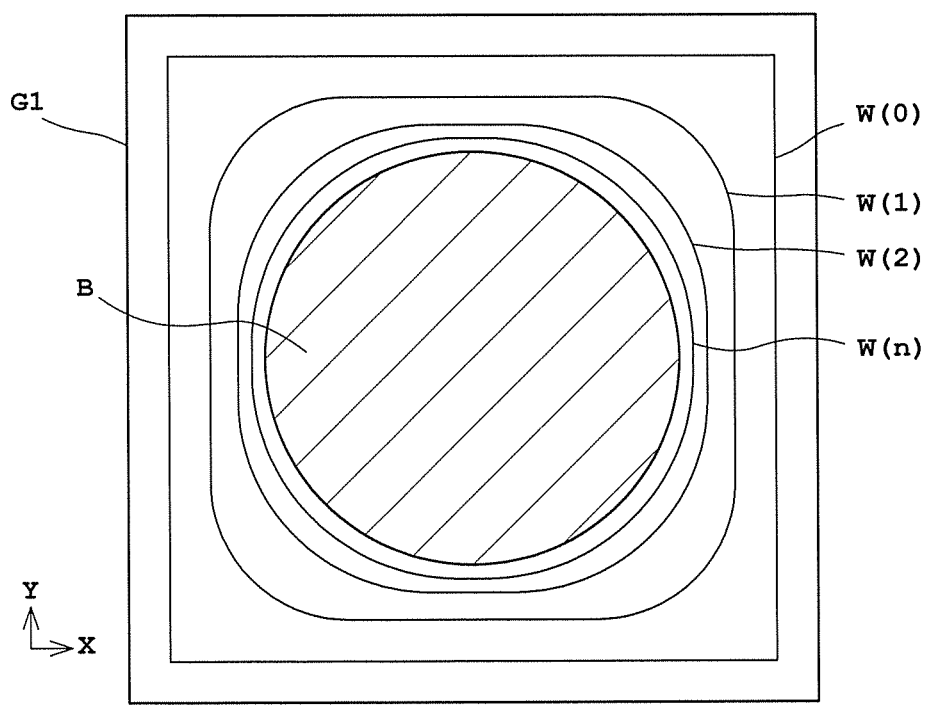
FIG. 4 is an explanatory view of a dynamic contour model.

As illustrated in FIG. 4, in the contour extraction, an initial contour W(0) is set so as to surround the breast B of the subject M largely in the two-dimensional reconstruction image G1, and the contour extraction is repeatedly conducted, whereby a contour W(1), a contour W(2), a contour W(3), and contour W(n) are obtainable in turn. With a first contour extraction process, the first shape of the contour Wa corresponds to the contour W(0), and the new the second shape of the contour Wb corresponds to the contour W(1). With a second contour extraction process, the first shape of the contour Wa corresponds to the contour W(1), and the new the second shape of the contour Wb corresponds to the contour W(2).

Figure 5:
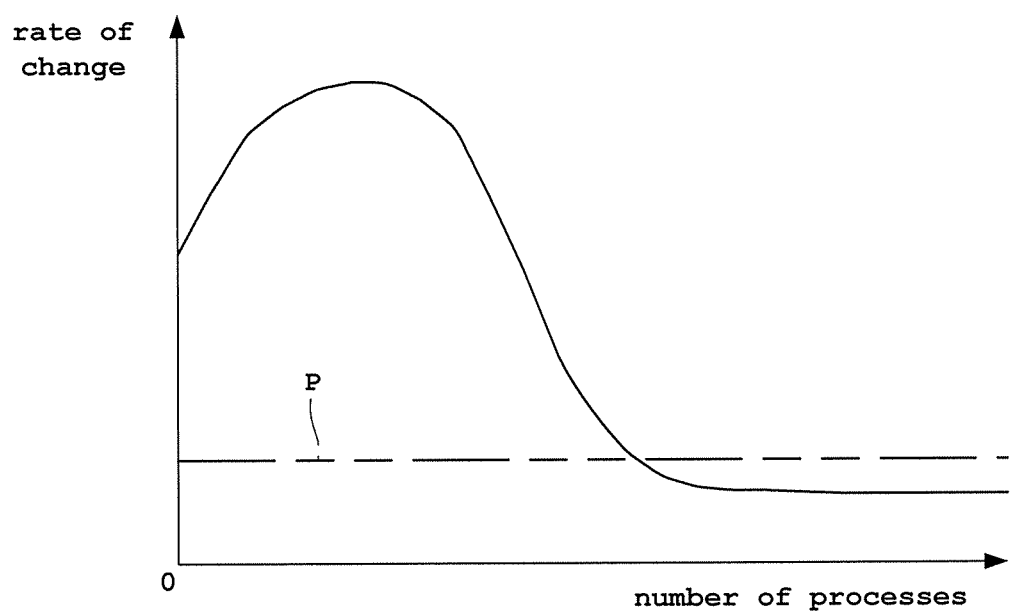
FIG. 5 illustrates a relationship between the number of processes for contour extraction and a rate of change.

The following describes the completion determination that determines whether or not the new second shape of the contour Wb generated by the contour extracting unit 41 is an appropriate shape of the contour. In the present embodiment, the completion determination is performed every one contour extraction. The rate of change Ra is used for the completion determination. The rate of change Ra is a ratio of the varied area S between the first shape of the contour Wa and the second shape of the contour Wb and the sum V of pixel values of the pixels in the varied area S. FIG. 5 illustrates a relationship of such a rate of change Ra.

FIG. 5 illustrates a relationship between the number of contour extraction processes T and the rate of change Ra. FIG. 5 includes a horizontal axis indicating the number of contour extraction processes T repeatedly performed, and a longitudinal axis indicating the rate of change Ra. When the contour extraction is repeatedly performed (i.e., when the number of processes increases), the following tendency is observed. That is, the contour W(n) is gradually close to the contour of the breast B of the subject M as in FIG. 4, and accordingly, the rate of change Ra in FIG. 5 temporarily increases and thereafter decreases to be stabilized around a given value. Performing the contour extraction by the number of processes T at which the rate of change Ra is stabilized around the given value achieves the shape of the contour with high accuracy.

The following describes in detail the characteristic that the rate of change Ra is stabilized within a substantially equal value every time regardless of data on the two-dimensional reconstruction images G1. During the contour extraction, a pixel value gradient generated in a boundary of an accumulation amount of RI contained in the radiopharmaceutical into the breast B (skin of the breast B) and noise of pixels outside the breast B are searched in the two-dimensional reconstruction image G1 to extract the shape of the contour of the breast B. The noise of pixels around the breast B is caused by scattered radiation from the breast B or the trunk. An amount of scattered radiation is closely related to the accumulation amount of RI in the breast B. Moreover, a variation S in contour area in one-time contour extraction process becomes small as the pixel value gradient increases toward the contour of the breast B. From the above, the rate of change Ra in one contour extraction has the characteristic to be stabilized within a substantially equal value every time regardless of data on the two-dimensional reconstruction images (slice pieces) G1. With the characteristic, the threshold P is pre-set from a plurality of pieces of sample data obtained in advance. As a result, the contour extraction is automatically performable by the appropriate number of processes T for each of the two-dimensional reconstruction images G1.

In addition, some thresholds P are pre-set in the storage units 21 and 33 and the like depending on imaging conditions such as a requirement of the apparatus 1, a size of a patient's trunk, and an administration condition of the radiopharmaceutical. The repetitive controller 39 selectively reads out and uses the conditions from the storage units 21 and 33 and the like. This allows automatic contour extraction by the appropriate number of processes T depending on the imaging conditions.

Figure 6:
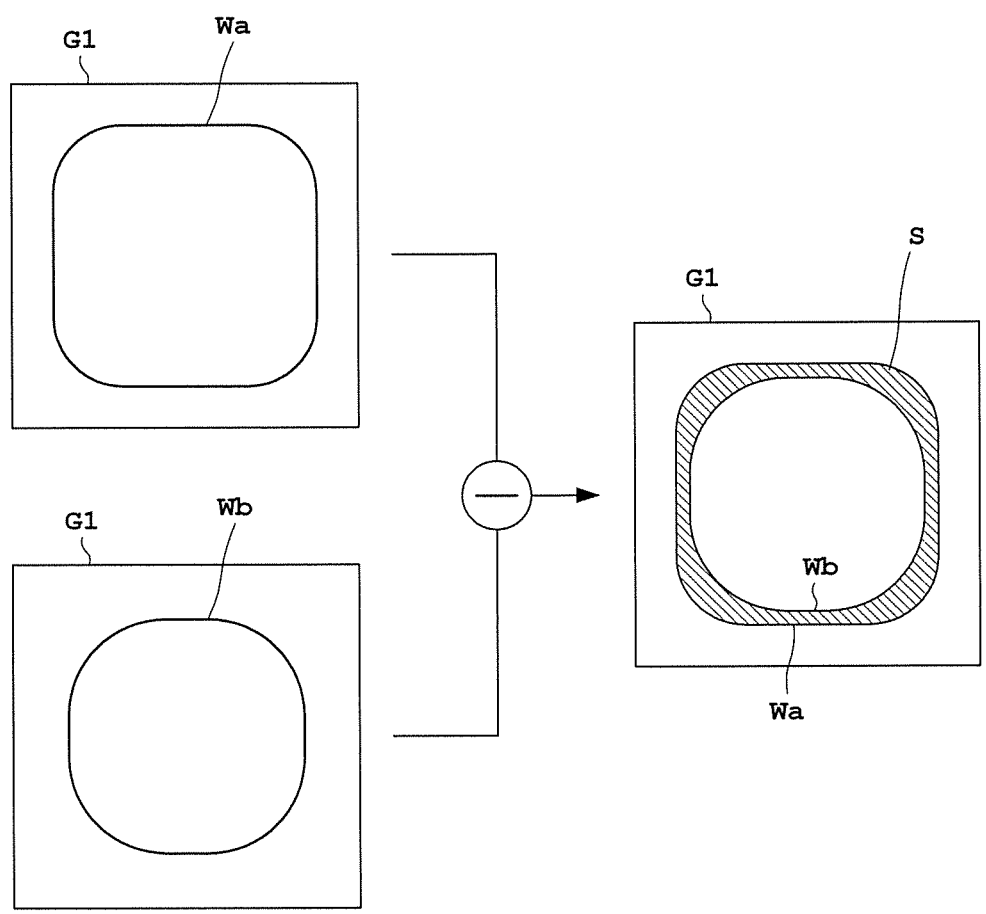
FIG. 6 is an explanatory view of how to calculate a varied area and the sum of pixel values.

As noted above, the rate of change Ra is calculated from the varied area calculating unit 43, the pixel value sum calculating unit 45, and the change rate calculating unit 47. That is, as illustrated in FIG. 6, the varied area calculating unit 43 calculates the varied area S between the first shape of the contour Wa and the second shape of the contour Wb. The pixel value sum calculating unit 45 calculates the sum V of pixel values of the pixels in the varied area S. The change rate calculating unit 47 calculates the rate of change Ra (=S/V) as a ratio of the varied area S and the sum V.

The completion determining unit 49 determines whether or not the rate of change Ra is smaller than the pre-set threshold P. The repetitive controller 39 performs control to set the second shape of the contour Wb as the first shape of the contour Wa when the completion determining unit 49 determines that the rate of change Ra is larger than the threshold P. For instance, when the second shape of the contour Wb corresponds to a contour W(1) in FIG. 4, the first shape of the contour Wa is set as the contour W(1) in FIG. 4. Then, the repetitive controller 39 performs control to operate again the contour extracting unit 41, the varied area calculating unit 43, the pixel value sum calculating unit 45, the change rate calculating unit 47, and the completion determining unit 49. Moreover, the repetitive controller 39 outputs the two-dimensional contour image Gr1 containing the second shape of the contour Wb when the completion determining unit 45 determines that the rate of change Ra is smaller than the threshold P.

On the subsequent stage of the contour determining unit 35, provided is the contour image collecting unit 37 that collects the two-dimensional contour images Gr1 to output the three-dimensional contour image Gr. The repetitive controller 39 reads out the two-dimensional reconstruction images GI in turn that form the three-dimensional reconstruction image G to generate a two-dimensional contour image Gr1 from the two-dimensional reconstruction images G1, thereby generating a three-dimensional contour image Gr from a plurality of two-dimensional contour images Gr1.

Here, the initial contour W(0) and the threshold P in FIG. 4 are pre-set by the operator via the input unit 19. Moreover, the completion determining unit 49 may output the two-dimensional contour image Gr1 containing the second shape of the contour Wb when the rate of change Ra is equal to the threshold P (Ra=P). Alternatively, the contour extracting unit 41 and the like may operate again.

The following describes operation of the mammography PET apparatus 1. Firstly, overall operation of the mammography PET apparatus 1 is to be described, and secondary, operation of the contour image generating unit 9 in the mammography PET apparatus 1 is to be described.

Overall Operation of Mammography PET Apparatus

The following describes operation of the mammography PET apparatus 1. The radiopharmaceutical is administered to the subject M, and the subject M is placed on the mammography PET apparatus 1. At this time, the breast B of the subject M as the imaging target is disposed inside of the γ-ray detectors 7 of the detector unit 3 in a ring shape. Then γ-rays are emitted from the breast B of the subject M. The emitted γ-rays are divided into two beams at a straight angle opposite to each other. The detector unit 3 detects the two beams of γ-rays. The data collecting unit 5 collects an event indicating detection of two beams of γ-rays with two γ-ray detectors 7 in a given period of time as the emission data E1.

Then the absorption correcting unit 11 performs absorption correction to the emission data E1 collected by the data collecting unit 5. The absorption correction is performed with the three-dimensional contour image Gr generated by the contour image generating unit 9. That is, the absorption correcting unit 11 performs absorption correction to the emission data E1 using the absorption map having the absorption coefficient preset in the contour of the three-dimensional contour image Gr being uniformly assigned. In this manner, emission data E2 subjected to the absorption correction is obtained.

The reconstruction unit 13 reconstructs the emission data E2 subjected to the absorption correction to a three-dimensional PET image Gp. The reconstructed three-dimensional PET image Gp is displayed on the display unit 17, and is stored in the storage unit 21. The image displayed on the display unit 17 may be any section in the three-dimensional PET image Gp. Moreover, when the absorption correcting unit 11 is included in the system model of the reconstruction unit 13, the reconstruction unit 13 performs image reconstruction and absorption correction to the emission data E1 to generate the three-dimensional PET image Gp.

Operation of Contour Image Generating Unit of Mammography PET Apparatus

Figure 7:
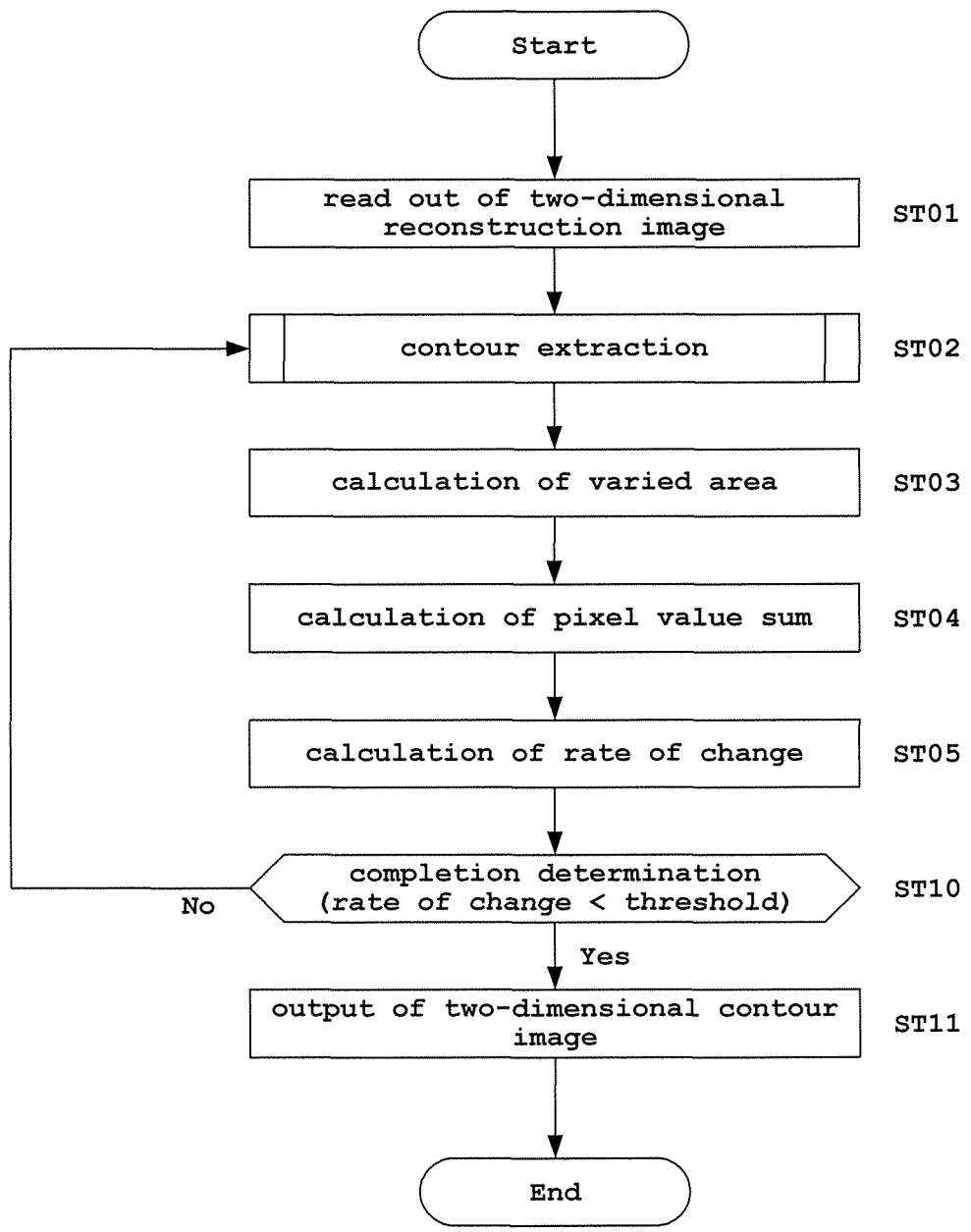
FIG. 7 is a flow chart illustrating operation of the contour image generating unit according to the Embodiment 1.

The following describes operation of the contour image generating unit 9, which is a characteristic of the present invention. FIG. 7 is a flow chart illustrating operation of the contour image generating unit 9 according to the Embodiment 1. In the contour image generating unit 9, the reconstruction unit 31 reconstructs the emission data E1 collected by the data collecting unit 5 to generate a three-dimensional reconstruction image G for the breast B of the subject M. The generated three-dimensional reconstruction image G is stored in the storage unit 33.

Step ST01: Read Out of Two-Dimensional Reconstruction Image

The repetitive controller 39 performs control to read out one two-dimensional reconstruction image G1 from a plurality of two-dimensional reconstruction images G1 (see FIG. 3) that form the three-dimensional reconstruction image G stored in the storage unit 33, and transmits the two-dimensional reconstruction image G1 to the contour extracting unit 41. Moreover, the repetitive controller 39 performs control to transmit the initial contour W(0) to the contour extracting unit 41 from the storage units 21 and 33 that store information on the initial contour W(0), the threshold P and the like, and to transmit the threshold P to the completion determining unit 49.

Step ST02: Contour Extraction

The contour extracting unit 41 performs one of the contour extraction processes in the obtained two-dimensional reconstruction image GI. The contour extraction processes are repeatedly performed by the contour extracting model (e.g., a level set method) to extract the new the second shape of the contour Wb from the pre-set the first shape of the contour Wa. In the two-dimensional reconstruction image G1 in FIG. 4, with the first contour extraction process, the first shape of the contour Wa is set to be the initial contour W(0), and the first contour extraction obtains the contour W(1) as the new second shape of the contour Wb.

Step ST03: Calculation of Varied Area

The varied area calculating unit 43 calculates the varied area S between the first shape of the contour Wa and the second shape of the contour Wb. The varied area S is calculated from a difference between the second shape of the contour Wb and the first shape of the contour Wa. FIG. 6 illustrates a diagonally shaded region as the varied area S.

Step ST04: Calculation of Pixel Value Sum

After the varied area calculating unit 43 calculates the varied area S, the pixel value sum calculating unit 45 calculates the sum V of pixel values of the pixels in the varied area S. That is, the pixel value sum calculating unit 45 calculates the sum (total sum) V of pixel values of the pixels in the varied area S like FIG. 6.

Step ST05: Calculation of Rate of Change

The change rate calculating unit 47 calculates a rate of change Ra (=S/V) as a ratio of the varied area S and the sum V.

Step ST10: Completion Determination (Rate of Change<Threshold)

The completion determining unit 49 determines whether or not the rate of change Ra is smaller than the pre-set threshold P. When the completion determining unit 49 determines that the rate of change Ra is larger than the threshold P, the repetitive controller 39 sets the second shape of the contour Wb as the first shape of the contour Wa. For instance, when the contour W(1) corresponds to the second shape of the contour Wb, the repetitive controller 39 sets the contour W(1) as the first shape of the contour Wa. Then, the repetitive controller 39 performs control to operate again the contour extracting unit 41, the varied area calculating unit 43, the pixel value sum calculating unit 45, the change rate calculating unit 47, and the completion determining unit 49. In other words, the repetitive controller 39 performs control to conduct again the above steps ST02 to ST10.

Step ST11: Output of Two-Dimensional Contour Image

When the completion determining unit 49 determines that the rate of change Ra is smaller than the threshold P (see FIG. 5), the repetitive controller 39 outputs the two-dimensional contour image Gr1 containing the second shape of the contour Wb.

In the steps ST01 to ST11 in FIG. 7, an shape of the contour is extracted from one two-dimensional reconstruction image G1 and the two-dimensional contour image Gr1 is outputted. Such a process is performed by the repetitive controller 39 to all or required number of two-dimensional reconstruction images G1 that form the three-dimensional reconstruction image G to output a plurality of two-dimensional contour images Gr1. The two-dimensional contour images Gr1 are each determined based on the threshold P. The contour extraction processes are performed automatically by the appropriate number of processes, and thus the two-dimensional contour images Gr1 have high accuracy. Then, the contour image collecting unit 37 collects the outputted two-dimensional contour images Gr1 to output the three-dimensional contour image Gr. Since the two-dimensional contour images Gr1 each include the shape of the contour extracted accurately, the three-dimensional contour image Gr to be outputted includes a shape of the contour with high accuracy.

With the aspect of the present embodiment, the contour extracting unit 41 of the contour image generating device 9 performs the one-time contour extraction to the two-dimensional reconstruction image G1 by the contour extracting model so as to extract the new second shape of the contour Wb from the first shape of the contour Wa set in advance. The completion determining unit 49 determines whether or not the rate of change Ra is smaller than the pre-set threshold P. The rate of change Ra is calculated as under. The varied area calculating unit 43 calculates the varied area S between the first shape of the contour Wa and the second shape of the contour Wb. The pixel value sum calculating unit 45 calculates the sum V of pixel values of the pixels in the varied area S. The change rate calculating unit 47 calculates the rate of change Ra as a ratio of the varied area S and the sum V. When the completion determining unit 49 determines that the rate of change Ra is larger than the threshold P, the repetitive controller 39 performs control to set the second shape of the contour Wb as the first contour Wa, to operate the contour extracting unit 41 and the like again. When the completion determining unit 49 determines that the rate of change Ra is smaller than the threshold P, the repetitive controller 39 performs control to output the two-dimensional contour image Gr1 containing the second shape of the contour Wb.

Specifically, the rate of change Ra that corresponds to the ratio of the varied area S and the sum V of pixel values of the pixels contained in the varied area S has a characteristic to be stabilized within a substantially equal value at every time regardless of data on the two-dimensional reconstruction image G1. Such a characteristic is used for setting the threshold P in advance from a plurality of samples of data obtained in advance. The repetitive controller 39 performs control to output the two-dimensional contour image Gr1 containing the second shape of the contour Wb when the completion determining unit 49 determines that the rate of change Ra is smaller than the threshold P. This allows automatic extraction of the shape of the contour of the breast B of the subject M accurately by the appropriate number of processes T without any visual confirmation by the operator.

Moreover, the two-dimensional reconstruction image G1 is one of two-dimensional reconstruction images G1 forming a three-dimensional reconstruction image G subjected to the reconstruction (see FIG. 3), and that the repetitive controller 39 performs control to generate the three-dimensional contour image Gr from a plurality of outputted two-dimensional contour images Gr1. For instance, when the contour extraction is performed by a fixed number of processes T, the appropriate number of processes T is performed to one image, and a large or small number of processes T is performed to another image. Regarding this, the present embodiment achieves the two-dimensional contour image Gr1 by the appropriate number of processes T for every two-dimensional reconstruction image (slice piece) G1.

Figure 3:
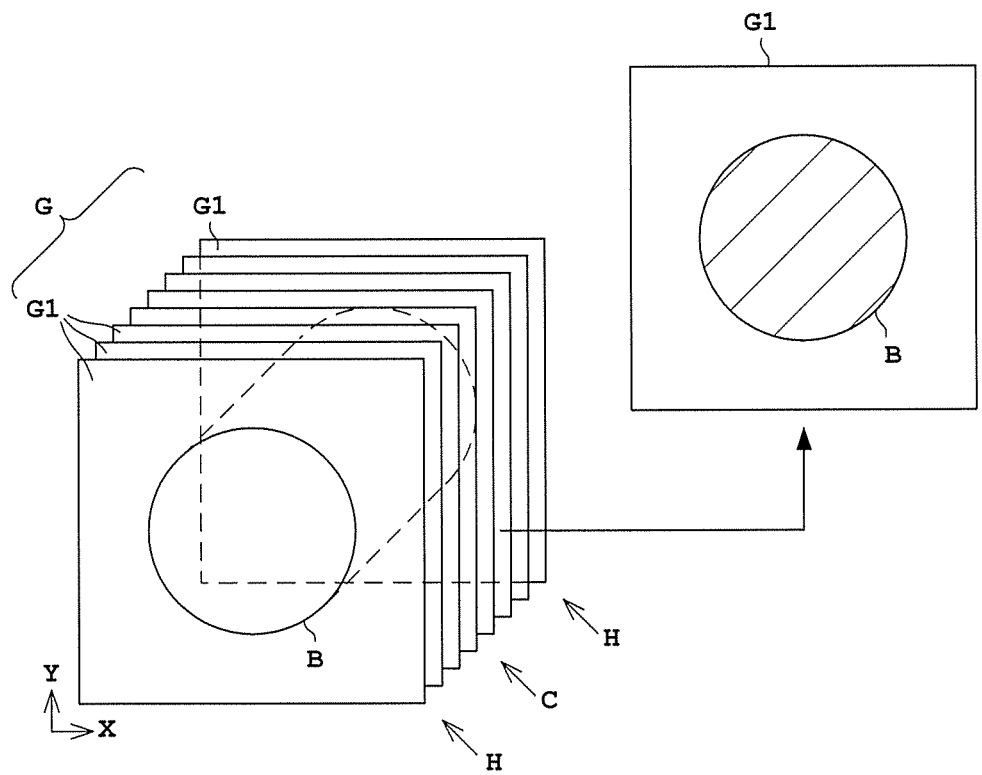
FIG. 3 is an explanatory view of a plurality of two-dimensional reconstruction images forming a three-dimensional reconstruction image.

As in FIG. 3, a two-dimensional reconstruction images GI at both ends denoted by numerals H each have a lower sensitivity than that of the two-dimensional reconstruction image G1 at the center denoted by a numeral C because of a configuration of the detector unit 3, and thus have a low statistical precision. Consequently, if the contour extraction is performed by the same number of processes T to the two-dimensional reconstruction image GI at the center denoted by the numeral C, a shape of the contour to be obtained has a low accuracy. With the present embodiment, the rate of change Ra is calculated to every two-dimensional reconstruction image (slice piece) G1 and completion determination is performed based on the threshold P. Accordingly, accurate extraction of the shape of the contour is performable not only to the two-dimensional reconstruction image GI at the center denoted by the numeral C but also to the two-dimensional reconstruction images G1 on the both ends denoted by the numerals H.

EMBODIMENT 2

Figure 8:
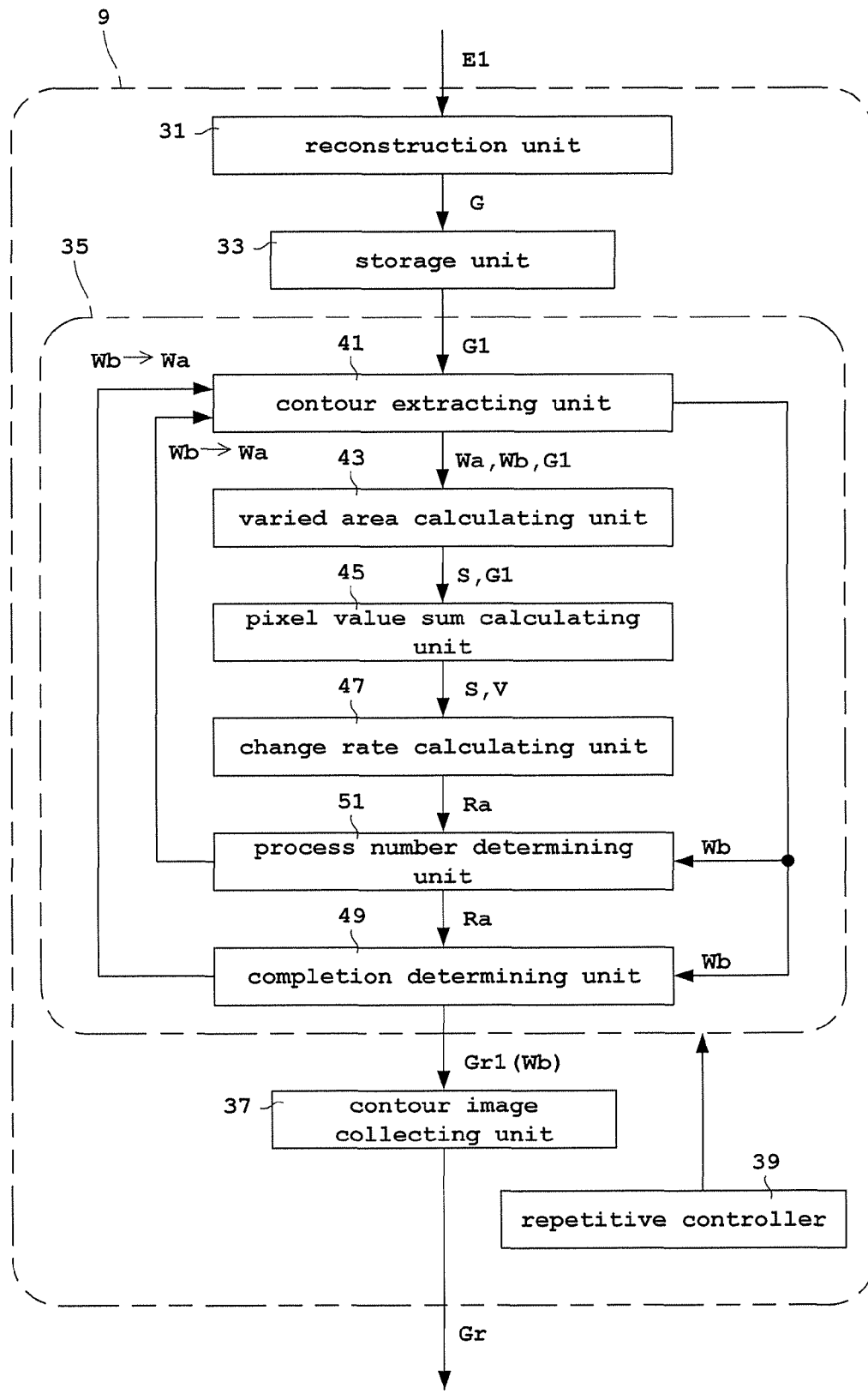
FIG. 8 illustrates a contour image generating unit according to Preferred Embodiment 2 of the present invention.

The following describes Embodiment 2 of the present invention with reference to drawings. FIG. 8 illustrates a configuration of a contour image generating unit 9 according to Preferred Embodiment 2. Here, description of the configuration common to that of Embodiment 1 is to be omitted.

In the contour image generating unit 9 in Embodiment 1, the completion determining unit 49 performs determination every one contour extraction process. In contrast to this, in Embodiment 2, the completion determining unit 49 performs determination every plural numbers of contour extraction process.

In addition to the elements of Embodiment 1, the contour image generating unit 9 of the present embodiment includes a process number determining unit 51 that counts the number of contour extraction processes T to determine whether or not the number of processes T reaches a break number of times K. For instance, when it is assumed that the break number of times K is five, the process number determining unit 51 performs determination so as to count the number of contour extraction processes T with the contour extracting unit 41 and to repeat operation by the contour extracting unit 41, the varied area calculating unit 43, the pixel value sum calculating unit 45, and the change rate calculating unit 47 five times.

Operation of Contour Image Generating Unit in Mammography PET Apparatus

Figure 9:
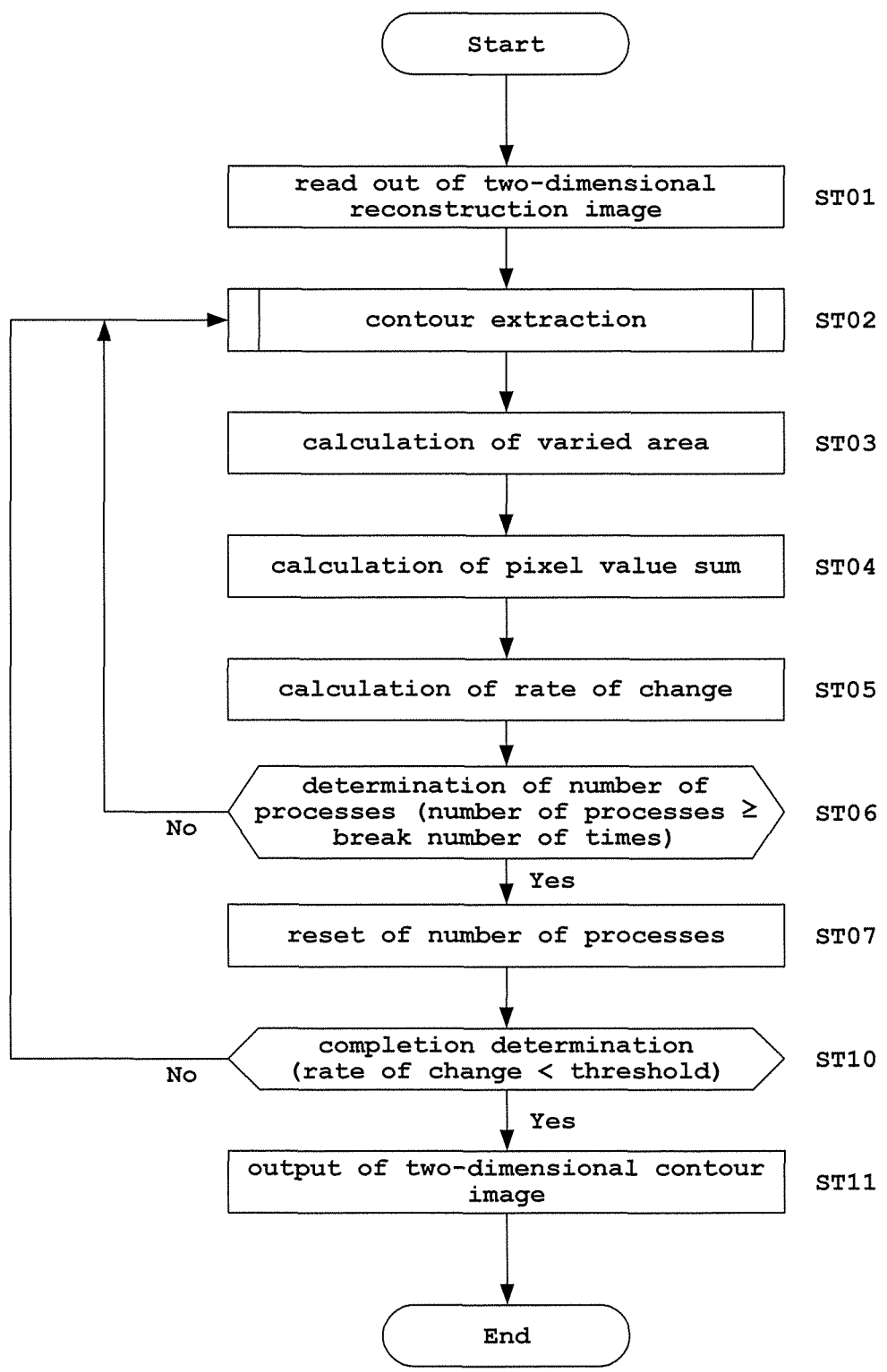
FIG. 9 is a flow chart illustrating operation of the contour image generating unit according to the Embodiment 2.

The following describes operation of the contour image generating unit 9 according to the present embodiment. FIG. 9 is a flow chart illustrating operation of the contour image generating unit 9 according to Embodiment 2. Here, description of the configuration common to that of Embodiment 1 is to be omitted appropriately.

Step ST01: Read out of Two-Dimensional Reconstruction Image

The repetitive controller 39 performs control to read out one two-dimensional reconstruction image G1 from a plurality of two-dimensional reconstruction images G1 (see FIG. 3) that form the three-dimensional reconstruction image G stored in the storage unit 33, and transmits the two-dimensional reconstruction image G1 to the contour extracting unit 41. Moreover, the storage units 21 and 33 store information on the initial contour W(0), the threshold P, the break number of times K and the like. The repetitive controller 39 performs control to read out the initial contour W(0), the threshold P, and the break number of times K to the contour extracting unit 41 from the storage units 21 and 33, and to transmit the initial contour W(0), the threshold P, and the break number of times K to the contour extracting unit 41, the completion determining unit 49, and the process number determining unit 51, respectively. Here, the number of processes T is "0" prior to process.

Step ST02: Contour Extraction Process

The contour extracting unit 41 performs one-time contour extraction in the obtained two-dimensional reconstruction image G1 by the contour extracting model (e.g., a level set method). That is, the contour extracting unit 41 extracts the contour W(1) as the second shape of the contour Wb from the initial contour W(0) as the first shape of the contour Wa.

Step ST03: Calculation of Varied Area

The varied area calculating unit 43 calculates the varied area S between the first shape of the contour Wa and the second shape of the contour Wb for every number of processes T. For instance, when the break number of times K is five, five varied areas S1 to S5 are calculated by calculating the varied area S for every number of processes T.

Step ST04: Calculation of Pixel Value Sum

The pixel value sum calculating unit 45 calculates the sum V of pixel values of the pixels in the varied area S for every number of processes T. For instance, when the break number of times K is five, five sums V1 to V5 are calculated by calculating the sum V of pixel values for every number of processes T.

Step ST05: Calculation of Rate of Change

The change rate calculating unit 47 calculates the rate of change Ra for every break number of times K, the rate of change Ra corresponding to a ratio of the sum of the varied area S and the total of the sum V. For instance, when the break number of times K is five as noted above, five varied areas S1 to S5 and five sums V1 to V5 are generated. Accordingly, the rate of change Ra is calculated as under: Ra=(S1+S2+S3+S4+S5)/(V1+V2+V3+V4+V5).

Step ST06: Determination of Number of Processes (Number of Processes≥Break Number of Times)

The process number determining unit 51 counts the number of contour extraction processes T to determine whether or not the number of processes T reaches the break number of times K. For instance, when the number of processes T is 1 (T=1), the process number determining unit 51 determines that the number of processes T fails to reach the break number of times K. The repetitive controller 39 performs control to set the second shape of the contour Wb as the first shape of the contour Wa when the process number determining unit 51 determines that the number of processes T fails to reach the break number of times K. Then, the repetitive controller 39 performs control to operate again the contour extracting unit 41, the varied area calculating unit 43, the pixel value sum calculating unit 45, the change rate calculating unit 47, and the process number determining unit 51. That is, the repetitive controller 39 performs the steps ST02 to ST06 again.

Step ST07: Reset of Number of Processes

When the process number determining unit 51 determines that the number of processes T reaches the break number of times K (i.e., (T≥K), the repetitive controller 39 performs control to reset the number of processes T (T=0). Then, the repetitive controller 39 performs determination by the completion determining unit 49 in the step ST10.

Step ST10: Completion Determination

The completion determining unit 49 determines whether or not the rate of change Ra is smaller than the pre-set threshold P. When the completion determining unit 49 determines that the rate of change Ra is larger than the threshold P, the repetitive controller 39 performs control to set the second shape of the contour Wb as the first shape of the contour Wa. When the second shape of the contour Wb is the contour W(5), the repetitive controller 39 performs control to set the contour W(5) as the first shape of the contour Wa. Then, the repetitive controller 39 performs control to operate again the contour extracting unit 41, the varied area calculating unit 43, the pixel value sum calculating unit 45, the change rate calculating unit 47, and the completion determining unit 49. That is, the repetitive controller 39 performs the steps ST02 to ST10 again.

Step ST11: Output of Two-Dimensional Contour Image

When the completion determining unit 49 determines that the rate of change Ra is smaller than the threshold P, the repetitive controller 39 performs control to output the two-dimensional contour image Gr1 containing the second shape of the contour Wb.

The process in steps ST01 to ST11 in FIG. 9 are performed by the repetitive controller 39 to all or required number of two-dimensional reconstruction images G1 that form the three-dimensional reconstruction image G to output a plurality of two-dimensional contour images Gr1.

Figure 10:
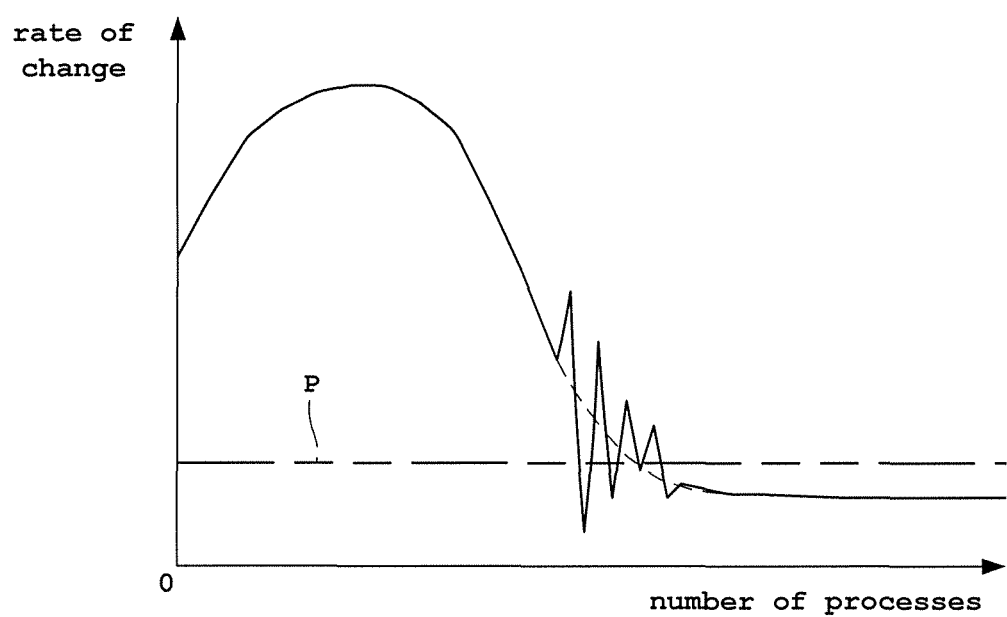
FIG. 10 illustrates a relationship between the number of processes for contour extraction and a rate of change.

In a relationship between the number of contour extraction processes T and the rate of change Ra as in FIG. 10 in the present embodiment, the rate of change Ra may increase and decrease for one-time process T because of the statistical noises in the two-dimensional reconstruction image G1. In this case, if completion determination is performed for every number of processes T, the rate of change Ra temporarily decreases largely to be smaller than the threshold P, leading to completion of the contour extraction before the rate of change Ra is stabilized. Regarding this, in the present embodiment, the process number determining unit 51 is provided for performing determination for every break number of times K, i.e., for each of plural numbers of processes T without any completion determination for every one-time process. Moreover, the change rate calculating unit 47 calculates the rate of change Ra that corresponds to the ratio of the sum of the varied areas S and the sum V of the pixel values for every break number of times K. As a result, the completion determining unit 49 performs determination with the rate of change Ra calculated as an average value for every break number of times K. Consequently, this prevents completion of the contour extraction before the rate of change Ra is stabilized by a variation in rate of change Ra for every one-time process, leading to generation of the two-dimensional contour image Gr1 by the appropriate number of processes T.

Moreover, in the present embodiment, the change rate calculating unit 47 calculates the rate of change Ra for every number of processes T. Alternatively, the change rate calculating unit 47 may be provided between the process number determining unit 51 and the completion determining unit 49 for calculating the rate of change Ra when the process number determining unit 51 determines that the number of processes T reaches the break number of times K. Moreover, the position of the process number determining unit 51 in FIG. 8 is not limitative when the rate of change Ra every break number of times K is able to be calculated.

The present invention is not limited to the foregoing examples, but may be modified as follows.

(1) The break number of times K in Embodiment 2 may be variable. That is, when the number of processes T reaches the break number of times K, a next break number of times K may be set different from the previous break number of times K. For instance, in the number of processes T having a large difference between the rate of change Ra and the threshold P, a large number of processes T is set as the break number of times K. In contrast to this, in the number of processes T having a small difference between the rate of change Ra and the threshold P, the small number of processes T is set as the break number of times K. This allows extraction of the shape of the contour accurately by the appropriate number of processes T while the number of completion determination is decreased.

Moreover, the break number of times K may be set small as the number of processes T reaches the break number of times K. That is, when the number of processes T reaches the break number of times K, a next break number of times K is set smaller than or equal to the previous break number of times K. This allows extraction of the shape of the contour accurately by the appropriate number of processes T while the number of completion determination is decreased.

(2) The break number of times K in Embodiment 2 may be constant. This allows simple completion determination under the same condition.

(3) In the embodiments and the modifications mentioned above, the contour image generating unit 9 generates the three-dimensional contour image Gr from the three-dimensional reconstruction images G. However, the contour image generating unit 9 may generate the two-dimensional contour image Gr1 from the two-dimensional reconstruction image G1.

(4) In the embodiments and the modifications mentioned above, the mammography PET apparatus 1 has been described as one example of nuclear medicine diagnosis apparatus. However, this is not limitative. For instance, the nuclear medicine diagnosis apparatus is applicable to a modality such as a PET apparatus for head, a PET/CT apparatus for head, and a PET/SPECT apparatus for head that image the head of the subject M. That is, the present invention is applicable to a nuclear medicine diagnosis apparatus that images an object as a substantially single absorber.

REFERENCE SIGN LIST

1 . . . mammography PET apparatus
3 . . . detector unit
5 . . . data collecting unit
7 . . . γ-ray detector
9 . . . contour image generating unit
15 . . . main controller
31 . . . reconstruction unit
39 . . . repetitive controller
41 . . . contour extracting unit
43 . . . varied area calculating unit
45 . . . pixel value sum calculating unit
47 . . . change rate calculating unit
49 . . . completion determining unit
51 . . . process number determining unit
M . . . subject
B . . . breast
E1 . . . emission data
G . . . three-dimensional reconstruction image
G1 . . . two-dimensional reconstruction image
Wa . . . first shape of the contour
Wb . . . second shape of the contour
W(0), W(1), W(2), . . . , W(n) . . . contour
S (S1, S2, S3 to Sn) . . . varied area
V (V1, V2, V3 to Vn) . . . sum of pixel value of pixels in varied area
Ra . . . rate of change
P . . . threshold
Gr1 . . . two-dimensional contour image
Gr . . . three-dimensional contour image
K . . . break number of times
T . . . number of processes

The invention claimed is:

1. A contour image generating device, comprising:
one or more processors, configured to:
perform one of contour extraction processes that are repeatedly performed by a contour extracting model to a two-dimensional reconstruction image of a subject obtained through detection of radiation emitted from the subject to extract a new second shape of a contour from a first shape of the contour set in advance;
calculate a varied area between the first shape of the contour and the second shape of the contour;
calculate a sum of pixel values of pixels contained in the varied area;
calculate a rate of change that corresponds to a ratio of the varied area and the sum;
determine whether or not the rate of change is smaller than a threshold set in advance; and
perform control to set the second shape of contour as the first shape of contour and to perform control so that the performance of one of contour extraction processes is repeated when the rate of change is determined to be larger than the threshold, and perform control to output two-dimensional contour image each containing the second shape of the contour when the rate of change is determined to be smaller than the threshold.

2. The contour image generating device according to claim 1, wherein the one or more processors are further configured to:
count the number of contour extraction processes to determine whether or not the number of processes reaches a break number of times;
calculate the rate of change for every break number of times that corresponds to a ratio of a total sum of the varied area and the sum;
perform control to set the second shape of the contour as the first shape of the contour and to perform control so that the performance of one of contour extraction processes is repeated when the number of processes are determined to fail to reach the break number of times and perform control to reset the number of processes and determine whether or not the rate of change is smaller than the threshold when the number of processes is determined to reach the break number of times; and perform control to set the second shape of the contour as the first contour and to perform control so that the performance of one of contour extraction processes is repeated when the rate of change is determined to be larger than the threshold.

3. The contour image generating device according to claim 2, wherein the break number of times is variable.

4. The contour image generating device according to claim 3, wherein
the break number of times decreases as the number of processes reaches the break number of times.

5. The contour image generating device according to claim 2, wherein the break number of times is constant.

6. The contour image generating device according to claim 1, wherein
the two-dimensional reconstruction image is one of two-dimensional reconstruction images forming a three-dimensional reconstruction image subjected to reconstruction, and
the one or more processors are further configured to perform control to generate the three-dimensional contour image from a plurality of the outputted two-dimensional contour images.

7. A nuclear medicine diagnosis apparatus, comprising:
a detector unit that includes a plurality of detectors arranged in a ring shape and detects radiation emitted from a subject;
a data collecting unit, including at least a coincidence circuit, that collects emission data in accordance with the radiation detected with the detector unit;
one or more processors, configured to:
reconstruct the emission data to obtain a two-dimensional reconstruction image;
perform one of contour extraction processes that are repeatedly performed by a contour extracting model to the two-dimensional reconstruction image to extract a new second shape of a contour from a first shape of the contour set in advance;
calculate a varied area between the first shape of the contour and the second shape of the contour;
calculate the sum of pixel values of pixels contained in the varied area;
calculate a rate of change that corresponds to a ratio of the varied area and the sum;
determine whether or not the rate of change is smaller than a threshold set in advance; and
perform control to set the second shape of contour as the first shape of contour and to perform control so that the performance of one of contour extraction processes is repeated when it is determined that the rate of change is larger than the threshold, and that performs control to output two-dimensional contour image each containing the second shape of the contour when the rate of change is determined to be smaller than the threshold.

* * * * *